United States Patent [19]
Hoffmann et al.

[11] Patent Number: 6,017,725
[45] Date of Patent: Jan. 25, 2000

[54] CYTOLOGICAL FIXATIVE AND DEHYDRATING AGENT FOR TREATING HISTOLOGICAL AND CYTOLOGICAL TISSUE

[75] Inventors: Ross W. Hoffmann, Crestwood; Thyparambil C. Mathew, Louisville, both of Ky.

[73] Assignee: AAPER Alcohol and Chemical Company, Shelbyville, Ky.

[21] Appl. No.: 09/136,775

[22] Filed: Aug. 19, 1998

Related U.S. Application Data

[60] Provisional application No. 60/056,225, Aug. 21, 1997.
[51] Int. Cl.⁷ .................................. G01N 1/30; G01N 1/36
[52] U.S. Cl. ........................................ 435/40.5; 435/40.52
[58] Field of Search ................................ 435/40.5, 40.52; 252/364

[56] References Cited

U.S. PATENT DOCUMENTS

| | | | |
|---|---|---|---|
| 3,663,243 | 5/1972 | Stryker et al. | 106/14.5 |
| 4,300,243 | 11/1981 | Baumgartner | 623/11 |
| 4,911,915 | 3/1990 | Fredenburgh | 435/40.52 |

*Primary Examiner*—Kathleen K. Fonda
*Assistant Examiner*—Marjorie A. Moran
*Attorney, Agent, or Firm*—Middleton & Reutlinger; John F. Salazar; Charles G. Lamb

[57] ABSTRACT

A cytological fixative and dehydrating agent used for treating histological and cytological tissues for pathological diagnoses consists of a blend of from about 11 to 21% ethyl alcohol, from about 35 to 45% methyl alcohol and from about 40 to 50% by weight isopropyl alcohol. The treated tissue is subjected to further processing to render the cells in the tissue stable prior to placing the tissue upon a glass slide for pathological examination.

6 Claims, No Drawings

CYTOLOGICAL FIXATIVE AND DEHYDRATING AGENT FOR TREATING HISTOLOGICAL AND CYTOLOGICAL TISSUE

This application claims the benefit of U.S. Provisional Application No. 60/056,225, filed Aug. 21, 1997.

BACKGROUND OF THE INVENTION

The present invention relates to a dehydrating agent for use in the processing of histological or cytological samples and more particularly relates to a novel combination of alcohols as fixative/dehydrating agents in the processing of histological or cytological samples.

The processing of tissue samples for pathological diagnosis requires a high quality conditioning of the tissue samples for attachment to glass slides which will be reviewed in the pathological diagnosis. In the processing of tissues for glass slides, the tissues are clinically removed from a patient and placed in a container which often contains a fixative and is then transported to the lab for further treatment or conditioning. The chemical reagents used as fixatives are those which will preserve the tissue components in a life-like manner. The tissue received in the fixative filled container are then generally cut into small sections, usually from 3 to 5 mms in thickness, and placed into vented, plastic cassettes. These cassettes are then placed into a tissue processor where they are subjected to a series of chemical reagents wherein the tissue, after being fixed, will be dehydrated, cleared and infiltrated generally with paraffin. The dehydrating step involves the removal of aqueous and some of the liquid tissue fluids with dehydrating agents. The clearing step involves the use of selected fluids to remove the dehydrating agent. In the infiltration with paraffin, the infiltration medium provides cellular support thereby enabling easy cutting of the tissue into sections for placement upon a slide, enabling pathologists the best possible specimen for diagnosing.

In the dehydrating step in the processing of tissue specimens, ethyl alcohol has been for many years the predominate liquid dehydrating agent. Moreover, ethyl alcohol has found use as a cytology fixative. In recent years, isopropyl alcohol and methyl alcohol have been suggested as alternatives to ethyl alcohol, but each of these alcohols used alone have proven to be unsatisfactory. However, U.S. Pat. No. 4,911,915 which issued to Fredenburgh on Mar. 27, 1990 teaches that a mixture of isopropyl alcohol and methyl alcohol in very specific ranges are equal to ethyl alcohol as a fixative and dehydrating agent in tissue specimen conditioning. Specifically, Fredenburgh teaches that a dehydrating agent consisting of from 30% to 45% by volume of methanol and 70 to 55% by volume of isopropyl alcohol works as well as ethyl alcohol in the processing of histological or cytological samples.

SUMMARY OF THE INVENTION

It is an object of the present invention to provide a novel liquid dehydrating agent for use in tissue processing.

It is a further object of the present invention to provide a novel cytology fixative for use in tissue processing.

It is another object of the present invention to provide a dehydrating agent and cytology fixative which is relatively inexpensive for use in tissue processing.

It is known in the preparation of tissue specimens for pathological diagnosis that methyl alcohol, ethyl alcohol, and isopropyl alcohol individually have distinct advantages and disadvantages as dehydrating agents. For example, ethyl alcohol and isopropyl alcohol have a tendency to harden tissue rapidly whereas methyl alcohol causes less hardening of the tissue specimen. However, methyl alcohol alone cannot be used in most closed processes as methyl alcohol is toxic. Moreover, methyl alcohol is not a universal dehydrant. And, methyl alcohol is not miscible with a number of clearing agents.

Isopropyl alcohol provides less shrinkage and hardening of the tissue specimens than ethyl alcohol and the major disadvantage for the use of isopropyl alcohol standing alone is that in certain processes utilizing nitrocellulose, nitrocellulose is insoluble in the isopropyl alcohol. Also in the preparing of staining solutions, most dyes are also not soluble in isopropyl alcohol.

As for the use of ethyl alcohol, ethyl alcohol has the advantages of being miscible in all proportions with water, it is not toxic and is fast acting. However, ethyl alcohol is relatively expensive and over long periods, excessive shrinkage and hardening of the tissue specimens occur.

However, it has been found that with a unique combination of ethyl alcohol, methyl alcohol and isopropyl alcohol, specifically any combination which includes from 11 to 21% ethyl alcohol, from 35 to 45% methyl alcohol, and, from 40 to 50% isopropyl alcohol a superior cytological fixative and dehydrating agent is obtained wherein the advantages of each of the alcohols is maximized and the disadvantages minimized. And, preferably the ethyl alcohol is from 11 to 21%, the methyl alcohol is from 39 to 41% and the isopropyl alcohol is from 43 to 45% by weight.

Additional objects and advantages of the present inventive dehydrating agent will become apparent to those skilled in the art upon consideration of the following detailed description including examples of the use of cytological fixatives and dehydrating agents of the present invention.

DETAILED DESCRIPTION OF THE PREFERRED EMBODIMENTS

In the preparation of a tissue specimen for pathological diagnosis, the tissue is placed into a container including a dehydrating agent and cytology fixative solution including a blend of alcohols consisting of methyl alcohol, ethyl alcohol and isopropyl alcohol wherein the methyl alcohol is from 35 to 45% by weight, the ethyl alcohol is from 11 to 21% by weight and the isopropyl alcohol is from 40 to 50% by weight. Preferably, the methyl alcohol is from 39 to 41% by weight, the ethyl alcohol is from 11 to 21% by weight, and the isopropyl alcohol is from 43 to 45% by weight. Since these tissue specimens are not firm and cohesive enough for sectioning, they are infiltrated with a supporting medium, usually paraffin, to render the cells stable thereby holding the cells and intracellular structures in their proper relationship one to another. In infiltrating the tissue specimen, the aqueous solution of the alcohol blend and any water remaining in the tissue which are immiscible with paraffin or the like, are removed. Thus, a paraffin solvent, such as xylene, toluene, and the like, which is miscible with both the alcohol blend and the paraffin infiltrate, the paraffin solvent, referred to as a clearing agent, is then used to remove the alcohol mixture. Paraffin or another infiltrating agent is then applied to the specimen and the specimens are then firm enough to be cut into relative thin sections of from about 3 to 5 mms in thickness and affixed to glass slides for pathological diagnosis.

The following example is given to illustrate the present invention.

EXAMPLE 1

A tissue specimen for histological and cytological examination is immersed into a fixation/dehydrating agent consisting of 16% ethyl alcohol, 40% methyl alcohol and 44% isopropyl alcohol. The resulting specimen is then further processed wherein the fixation/dehydrating agent is removed by subjecting the tissue to xylene, then adding paraffin and a staining dye. The tissue specimen is then cut into sections having a thickness of from 3 to 5 mm and placed upon a glass slide for pathological diagnosis. The resulting specimen which had been treated with the alcohol combination is relatively wrinkle free, pliable, and exhibits very little shrinkage.

EXAMPLES 2–12

Examples 2–12 are prepared in the same manner as Example 1 except the concentrations of alcohols in each of the Examples is varied. The resulting specimens for pathological diagnosis exhibit different characteristics depending upon the alcohol or alcohol blend.

TABLE I

| SAMPLE | ALCOHOL BLEND | CHARACTERISTICS OF TISSUE FOR PATHOLOGICAL DIAGNOSIS |
|---|---|---|
| 2 | 100% methyl | Tissue is relatively soft |
| 3 | 100% ethyl | Tissue shrank and is relatively hard |
| 4 | 100% isopropyl | Tissue has pungent odor and solubility problems with staining dye |
| 5 | 5% ethyl, 45% methyl, 44% isopropyl | Tissue is relatively soft |
| 6 | 11% ethyl, 45% methyl, 44% isopropyl | Tissue substantially the same as Example 1 |
| 7 | 21% ethyl, 39% methyl, 40% isopropyl | Tissue substantially the same as Example 1 |
| 8 | 20% ethyl, 35% methyl, 45% isopropyl | Tissue substantially the same as Example 1 |
| 9 | 10% ethyl, 45% methyl, 45% isopropyl | Tissue is soft |
| 10 | 30% ethyl, 20% methyl, 50% isopropyl | Tissue shrank and relatively hard |
| 11 | 20% ethyl, 20% methyl, 60% isopropyl | Tissue substantially the same as Example 4 |
| 12 | 15% ethyl, 20% methyl, 65% isopropyl | Tissue substantially the same as Example 4 |

It can be seen from the above Examples that Examples 1, 6, 7 and 8 produced a better tissue for pathological diagnosis than Examples 2–5 and 9–12.

It is to be understood that the invention is not to be limited to the specific example shown as the parameters set forth in the example may be varied by appropriate changes of the amounts of the individual alcohols used in the example.

What is claimed is:

1. A histological or cytological fixation and dehydrating agent comprising: from about 35 to 45% by weight of methyl alcohol, from about 11 to 21% by weight of ethyl alcohol, and from about 40 to 50% by weight of isopropyl alcohol.

2. The agent of claim 1 wherein said methyl alcohol is from 39 to 41% by weight, and said isopropyl alcohol is from 43 to 45% by weight.

3. The agent of claim 2, said ethyl alcohol is about 16% by weight.

4. A method for treating histological and cytological tissue to fix and dehydrate the tissue comprising the step of:

immersing the tissue in an alcohol mixture comprising from about 35 to 45% by weight of methyl alcohol, from about 11 to 21% by weight of ethyl alcohol, and from about 40 to 50% by weight of isopropyl alcohol.

5. The method of claim 4, wherein said methyl alcohol is from 39 to 41% by weight, and said isopropyl alcohol is from about 43 to 45% by weight.

6. The method of claim 5, said ethyl alcohol is about 16% by weight.

* * * * *

UNITED STATES PATENT AND TRADEMARK OFFICE
CERTIFICATE OF CORRECTION

PATENT NO. : 6,017,725
DATED : January 25, 2000
INVENTOR(S) : Hoffmann

It is certified that error appears in the above-identified patent and that said Letters Patent is hereby corrected as shown below:

Claim 1, col. 4, line 22, change "A histological or cytological fixation and dehydrating agent comprising:" to --A fixation and dehydrating agent for histological and cytological examination comprising --;
Claim 4, col. 4, line 33, change "fix" to --fixate --;
Claim 4, col. 4, line 38, delete "wherein" and change "is" to --being--.

Signed and Sealed this

Third Day of April, 2001

Attest:

NICHOLAS P. GODICI

Attesting Officer     Acting Director of the United States Patent and Trademark Office